United States Patent
Alnaimi et al.

(10) Patent No.: US 11,097,998 B1
(45) Date of Patent: Aug. 24, 2021

(54) PROCESS FOR PRODUCTION OF MIXED BUTANOL AND DIISOBUTENES AS FUEL BLENDING COMPONENTS

(71) Applicant: Saudi Arabian Oil Company, Dhahran (SA)

(72) Inventors: Essa I. Alnaimi, Dhahran (SA); Anas Saleh Al-Aqeeli, Dhahran (SA); Kareemuddin Shaik, Dhahran (SA); Hamad Saleh Al-Khaldi, Dhahran (SA); Ali M. Alshehri, Dammam (SA); Ahmed A. Alkhulaif, Dammam (SA); Faris Ibrahim Alnajran, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/806,847

(22) Filed: Mar. 2, 2020

(51) Int. Cl.
    *C07C 29/04* (2006.01)
    *C07C 29/82* (2006.01)
    (Continued)

(52) U.S. Cl.
    CPC ............ *C07C 29/04* (2013.01); *C07C 1/24* (2013.01); *C07C 5/2206* (2013.01); *C07C 29/82* (2013.01);
    (Continued)

(58) Field of Classification Search
    CPC .......... C07C 29/04; C07C 1/24; C07C 29/82; C07C 5/2206; C07C 11/08; C07C 31/12; C10L 10/10; C10L 2200/0423
    (Continued)

(56) References Cited

U.S. PATENT DOCUMENTS

| 1,283,435 | A | 10/1918 | Warren |
| 2,875,138 | A | 2/1959 | Altreuter et al. |

(Continued)

FOREIGN PATENT DOCUMENTS

| EP | 0196902 A2 | 10/1986 |
| EP | 2374780 A1 | 10/2011 |

OTHER PUBLICATIONS

Mahajani, Sanjay M., M. M. Sharma, and Tamarapu Sridhar. "Extractive hydration of n-butene with solid acid catalysts in the liquid phase and under supercritical conditions." Chemical engineering science 56.19 (2001): 5625-5633.

(Continued)

*Primary Examiner* — Deborah D Carr
(74) *Attorney, Agent, or Firm* — Leason Ellis LLP (57) ABSTRACT

Provided is a process for hydrating and oligomerizing a hydrocarbon feed comprising mixed olefins, by contacting the feed with water and a catalyst in a fixed bed reactor, wherein the catalyst hydrates mixed olefins to mixed alcohols and oligomerizes mixed olefins into oligomers; introducing the resulting stream into a first separator that separates an organic phase from an aqueous phase; introducing the organic phase into a second separator that separates unreacted olefins from mixed alcohols/oligomers; introducing the aqueous phase into a third separator that separates an alcohol-water azeotrope from water; introducing the second stream into a fourth separator that separates sec-butyl alcohol to produce a third stream comprising mixed butanols and oligomers and an SBA stream; f) mixing the third stream and a first portion of the SBA stream to produce a final product stream; and g) recycling a second portion of the SBA stream to the second separator.

21 Claims, 4 Drawing Sheets

(51) Int. Cl.
*C07C 1/24* (2006.01)
*C10L 10/10* (2006.01)
*C07C 5/22* (2006.01)
*C07C 31/12* (2006.01)
*C07C 11/08* (2006.01)

(52) U.S. Cl.
CPC ............... *C10L 10/10* (2013.01); *C07C 11/08* (2013.01); *C07C 31/12* (2013.01); *C10L 2200/0423* (2013.01)

(58) Field of Classification Search
USPC ....................................................... 568/894
See application file for complete search history.

(56) References Cited

U.S. PATENT DOCUMENTS

| | | |
|---|---|---|
| 3,203,872 A | 8/1965 | Baumann |
| 3,328,471 A | 6/1967 | Kronig et al. |
| 4,087,471 A | 5/1978 | Bowman et al. |
| 4,214,107 A | 7/1980 | Chang et al. |
| 4,236,034 A | 11/1980 | Aoshima et al. |
| 4,499,313 A | 2/1985 | Okumura et al. |
| 4,611,086 A | 9/1986 | Gueguen et al. |
| 4,902,385 A | 2/1990 | Osterburg |
| 5,105,023 A | 4/1992 | Marler et al. |
| 6,833,483 B2 | 12/2004 | Chuang et al. |
| 7,026,519 B2 | 4/2006 | Santiago Fernandez et al. |
| 7,125,474 B2 | 10/2006 | Beckmann et al. |
| 7,128,814 B2 | 10/2006 | Beckmann et al. |
| 7,141,707 B2 | 11/2006 | Beckmann et al. |
| 9,732,018 B2 | 8/2017 | Shaik et al. |
| 10,041,016 B2 | 8/2018 | Shaik et al. |
| 10,370,612 B2 | 8/2019 | Xu et al. |
| 2013/0104449 A1 | 5/2013 | Xu et al. |
| 2015/0225320 A1 | 8/2015 | Shaik et al. |

OTHER PUBLICATIONS

Kalamaras, Christos, et al. "SuperButol™—A novel high-octane gasoline blending component." Fuel 195 (2017): 165-173.

Tsai, Mao Jen et al., "Consider new technologies to replace MTBE: Clean fuels." Hydrocarbon processing (International ed.) 81.2 (2002): 81-88.

International Search Report & Written Opinion in Corresponding PCT Application No. PCT/US2021/020207 dated Jun. 11, 2021. 11 pages.

PROCESS FOR PRODUCTION OF MIXED BUTANOL AND DIISOBUTENES AS FUEL BLENDING COMPONENTS

FIELD OF THE INVENTION

The present disclosure relates to a process for the production of mixed alcohols (butanols) and butene oligomers. More specifically, the present disclosure relates to a process for hydrating and oligomerizing a feed stream comprising butene isomers to produce mixed butanols and butene oligomers. The process uses an enhanced azeotropic separation scheme to accommodate a large range of feedstocks and produce high quality products having utility as fuel additives.

BACKGROUND OF THE INVENTION

Although hydrocarbon fuels remain as the dominant energy resource for internal combustion engines, alcohols such as methanol and ethanol have also been used as fuels. Ethanol, the primary alcohol fuel, is commonly blended into gasoline in quantities of 5 to 10%. In fact, various fuels being produced today consist primarily of alcohols. For example, E-85 fuel contains 85% ethanol and 15% gasoline, and M-85 fuel has 85% methanol and 15% gasoline. While ethanol possesses excellent octane enhancement properties, there are several drawbacks to its use as a gasoline component, including: energy deficiencies (ethanol provides approximately 39% less energy than gasoline), high blending Reid Vapor Pressure (RVP) (at 10% of blending, the RVP=11 psi), and incompatibility with existing transportation facilities.

Lead (Pb) has historically been added to gasoline to increase its octane rating and thereby improve its antiknock properties. However, the use of lead in gasoline has now been eliminated in most countries for health and environmental reasons. Subsequently, methyl-tertiary-butyl-ether (MTBE) was commercially introduced as an octane enhancing component of gasoline in the United States and other countries in the late 1970s in order to meet the need for increased octane ratings in the absence of lead. Legal requirements on the minimum oxygen content of some gasolines, that were introduced in the 1990s as a means of reducing environmentally harmful exhaust emissions, encouraged a further increase in the concentration of MTBE in gasoline, which, by then, was being blended at up to 15% by volume.

However, concerns about the harmful effects of MTBE and its existence in groundwater, has led to a decline of its use in some countries, notably in the United States, where some states have actively legislated against its use. Thus, to meet today's performance and legal requirements, the fuel industry in the United States has replaced MTBE with fermented grain ethanol. Producing the necessary quantities of grain ethanol to replace MTBE, however, has proven problematic in specific regions, and the use of ethanol as a gasoline component has other drawbacks as discussed above.

Certain other alcohols (i.e., butanols), as well as butene oligomers (e.g., diisobutenes (DIBs)) can be used as combustible neat fuels, oxygenate fuel additives, or constituents in various types of fuels. The British Thermal Unit (BTU) content of butanols and diisobutenes is closer to the energy content of gasoline than either ethanol or methanol. Thus, butanols have been thought of as second generation fuel components after ethanols. In particular, 2-butanol (also known as sec-butanol) and tertiary butanol (also known as t-butanol) can be advantageous fuel components, as they have blending octane sensitivities and energy densities comparable to those of MTBE, and lower Reid vapor pressure (RVP) at 15% concentrations relative to comparable ethanol blends. Likewise, DIB is a non-oxygenated fuel component with several advantages over other fuel additives. For instance, DIBs have better anti-knock quality, higher research octane number (RON), and higher energy content compared with MTBE, as well as a lower RVP than ethanol, butanols, or MTBE.

Butanols can be produced via the hydration of butenes, a process that typically utilizes an acid catalyst. While the production of butanols via hydration of butenes is a commercially important process, it is typically very costly. DIBs are produced via the oligomerization/dimerization of butenes, in particular isobutene. The dimerization of isobutene is also generally performed using acid catalysts, such as sulfuric acid and hydrogen fluoride; however, these catalysts tend to be highly corrosive in nature.

Butanols and DIBs provide certain advantages over other existing fuel components. Thus, there have been efforts to design processes for converting mixed olefins into alcohols, especially butenes into butanols, while also oligomerizing part of the mixed olefins feed into oligomers such as DIBs.

U.S. Pat. No. 8,999,013 discloses method for contemporaneously dimerizing and hydrating a butene feed to produce mixed butanols in an acid catalyst. A mixed olefin feedstock is contacted with a dual phase catalyst in the presence of water to simultaneously hydrate and oligomerize the hydrocarbon feed to produce a product stream that includes oligomers (DIBs) and mixed butanols. The product stream is optionally dried and the dry product stream is then fed into a recovery column, where the butanol and DIB are separated from unreacted butenes. The butanol and DIB are then removed to form a final product.

U.S. Pat. No. 9,732,018 discloses a process for simultaneously hydrating and oligomerizing a hydrocarbon feed comprising mixed olefins, resulting in productions of mixed alcohols and DIBs. The process comprises contacting a hydrocarbon feed with a catalyst the hydrates and oligomerizes the mixed olefins to form mixed alcohols and DIB; separating the organic from aqueous phase, and introducing the organic phase into a separator where unreacted mixed butenes are separated from final product stream. The process also comprises introducing the aqueous phase into an azeotropic distillation unit where the alcohol-water azeotrope is distilled out of the aqueous phase and recycled back to the high-pressure separator.

Still, inefficiencies exist in known processes for simultaneous hydration and dimerization of mixed butenes. First, the prior art processes are limited in the ability to separate the butanol/DIB products from water due to difficulties in azeotropic separation. Moreover, introduction of a feed with high quantity of isobutene (>10-25%) into the prior art systems exerts significant duty energy in the cooler and reboiler of the separation column, which may lead to off-specification products with higher water quantity than recommended (0.5 wt %). Thus, the prior art processes are limited in the range of feedstock compositions that may be used.

There is thus a need for a process that not only allows for the contemporaneous hydration and oligomerization of mixed butenes to alcohols and oligomers—namely butanols and DIB, but also increases the conversion rate of butenes and produces on-specification product streams.

SUMMARY

The present disclosure provides a system and process for simultaneous hydration and oligomerization of mixed butenes in the presence of a catalyst to produce mixed butanols/diisobutene (DIB) compositions having utility as fuel additives, e.g. as oxygenates and octane enhancers to replace methyl tert-butyl ether (MTBE) and ethanol as a neat fuel. In some embodiments, the compositions comprise sec-butyl alcohol (SBA) and tert-butyl alcohol (TBA) as the principal products.

As mentioned above, a limitation of the prior art process is that introducing a feed with high quantity of isobutene (e.g., >10-20%) would exert significant duty energy on the system, causing off-specification products with higher water quantities than recommended (0.5 wt %). The process described herein solves this limitation by featuring an enhanced azeotropic distillation which permits better separation of water. The system and process described herein includes two improvements over the prior art: (a) an additional distillation unit which separates SBA from TBA; and (b) a step of recycling of SBA to enhance separation of the azeotrope comprising TBA and water. These improvements tilt the azeotropic distillation curve to extract water more easily. The process provides a technical advantage in that it permits the use of higher quantity of isobutene which, in turn, allows for use of a wider range of olefin feedstock compositions than in the prior art. For example, the mixed olefin feed may comprise 10 wt % or greater isobutene, 20 wt % or greater isobutene, and the like.

Thus, in one embodiment, the present disclosure provides a process for simultaneously hydrating and oligomerizing a hydrocarbon feed comprising mixed olefins, the process comprising the steps of: a) contacting the hydrocarbon feed with water and a catalyst in a fixed bed reactor, wherein the catalyst hydrates the mixed olefins to form mixed alcohols and oligomerizes at least a portion of the mixed olefins into oligomers, to produce a first stream comprising an organic phase and an aqueous phase; b) introducing the first stream into a first separator that separates the organic phase from the aqueous phase; c) introducing the separated organic phase from step (b) into a second separator that separates unreacted olefins from mixed alcohols and one or more oligomers to produce a second stream comprising mixed alcohols and one or more oligomers; d) introducing the separated aqueous phase from step (b) into a third separator that separates an alcohol-water azeotrope component from water; e) introducing the second stream from step (c) into a fourth separator that extracts sec-butyl alcohol (SBA) to produce an SBA stream, and a third stream comprising mixed butanols and one or more oligomers; f) mixing the third stream obtained in step (e) with a first portion of the SBA stream obtained in step (e) to produce a final product stream; and g) recycling a second portion of the SBA stream produced in step (e) to the second separator so help break the azeotropic layer in the second separator. In one embodiment, the catalyst present in the fixed bed reactor comprises an ion exchange resin catalyst.

In one embodiment, the final product stream comprises mixed butanols and diisobutene (DIB). In a currently preferred embodiment, the final product stream comprises tert-butanol (TBA), sec-butanol (SBA) and diisobutene (DIB).

In another embodiment, the mixed olefins comprise mixed butenes selected from the group consisting of 1-butene, 2-trans-butene, 2-cis-butene, isobutene and any combination thereof.

In another embodiment, the mixed alcohols produced in step (a) comprise mixed butanols selected from the group consisting of 1-butanol, 2-butanol (sec-butanol), iso-butanol, tert-butanol, and mixtures thereof.

In another embodiment, the process described herein further comprises the steps of adjusting a pressure and temperature of the hydrocarbon feed and adjusting a pressure and temperature of the water. In one representative embodiment, the pressure of the fixed bed reactor is between about 10-70 bar, and the temperature of the fixed bed reactor is between about 100-160° C.

The first separator may comprise a high-pressure separator configured to separate the organic phase from the aqueous phase. Alternatively, the first separator may comprise a high-pressure separator and a low pressure separator that are arranged in series with the low-pressure separator being downstream of the high-pressure separator, wherein each of the high and low-pressure separators is configured to separate the organic phase from the aqueous phase.

In one embodiment, the second separator comprises a debutenizer which removes unreacted butenes. In accordance with this embodiment, the process may further comprise the step of recycling the unreacted butenes from the debutenizer to the fixed bed reactor.

In one embodiment, the third separator comprises an azeotropic distillation column in which the alcohol-water azeotrope is distilled out of the aqueous phase and recycled back to the first separator and water is recycled back to the fixed bed reactor.

In another embodiment, the fixed bed reactor comprises a multi-stage reactor, with each stage having an individual feed line that receives the hydrocarbon feed and an individual exit line that communicates with a common line that delivers the first product stream to the first separator.

In another embodiment, the system described herein further utilizes an isomerization unit that is fluidly connected between the second separator and the fixed bed reactor and that receives the unreacted olefins from the second separator and serves to convert the unreacted olefins from a first isomer to a second isomer prior to introduction into the fixed bed reactor. In a particular embodiment, the isomerization unit comprises a 2-butenes to 1-butenes isomerization unit, wherein the first isomer comprises 2-butenes and the second isomer comprises 1-butenes.

In one embodiment, the process further comprises the step of combining the final product stream with a gasoline stream to produce a gasoline product with reduced Reid vapor pressure (RVP) and increased research octane number (RON) compared with the gasoline stream alone.

In another aspect, the present disclosure provides a method for preparing a gasoline composition, by providing a fuel grade gasoline; (i) providing an octane enhancing composition which comprises the final product stream that is prepared in accordance with the aforementioned process, and comprises diisobutene and mixed butanols; and (ii) combining the fuel grade gasoline and octane enhancing composition to form the gasoline composition.

Further embodiments and the full scope of applicability of the present disclosure will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

A more complete understanding of the invention and its many features and advantages will be attained by reference to the following detailed description and the accompanying drawing. It is important to note that the drawing illustrates only one embodiment of the present disclosure and therefore should not be considered to limit its scope.

DETAILED DESCRIPTION OF CERTAIN EMBODIMENTS

The present disclosure is directed to a system and process to produce high-purity, on-specification mixed butanol products, which are potential replacement oxygenates for MTBE and ethanol as fuel additives. According to the present disclosure, mixed butenes are simultaneously hydrated and oligomerized using water in the presence of a catalyst to produce mixed DIB and mixed butanols, especially sec-butyl alcohol (SBA) and tert-butyl alcohol (TBA) as the principal products. The process described herein features an enhanced distillation apparatus that accommodates a higher concentration of isobutene and wider range of olefin feedstocks as compared with the prior art process.

As described herein, the process and system of the present disclosure comprise (i) a hydration of butene isomers (i.e., 1-butene, trans-2-butene, isobutene and cis-2-butene) and a selective oligomerization (e.g., dimerization) of at least a portion of the isobutene in the presence of water, wherein the oligomerization and hydration reactions are implemented in same reactor; in combination with (ii) selective downstream separation techniques to provide for more efficient removal of water to generate improved products with on-specification properties.

Chemical Reactions and Definitions
Mixed Olefins (Butenes)

Mixed butenes have four structural isomers: 1-butene, 2-cis-butene, 2-trans-butene, and isobutene (also known as isobutylene).

Optionally, other low olefins, such as propylene ($H_2C$=CH—$CH_3$) and ethylene ($H_2C$=$CH_2$), can also be present in the feed as described below.

Diisobutenes (DIBs) or Isooctenes

Diisobutenes include two isomers: 2,4,4-trimethyl-1-pentene and 2,4,4-trimethyl-2-pentene.

Mixed Butanols

Mixed butanols include at least two of the following compounds: 1-butanol, 2-butanol (sec-butanol), t-butanol, and isobutanol.

Preferred embodiments of the present disclosure include mixtures of 2-butanol and t-butanol in any proportion as described below.

Hydration of Mixed Butenes

Processes for the hydration of butenes to butanols are commercially important reactions as the products have several important industrial applications. Generally, the hydration of mixed butenes is selected to only produce 2-butanol and t-butanol as illustrated in Schemes 1 and 2. However, the formation of other compounds is possible. Mixed butanols, primarily 2-butanol (sec-butanol) and t-butanol, can be used as oxygenative-type premium gasoline additives.

Scheme 1

Scheme 2

Other possible products that can be derived from the hydration of mixed butenes include but are not limited to etherification products of butanols and butenes or butanols itself. Butanols generally have good gasoline octane blending characteristics and can be used in combination as petroleum additives with other oxygenates, such as ethanol and MTBE.

Oligomerization (Dimerization)

Oligomerization of mixed butenes as described herein include oligomerization of all butene isomers, preferably oligomerization of isobutene and more preferably, the dimerization of isobutene as described in Scheme 3. The oligomerization fraction can be rich in dimers (isooctenes or DIBs) and can be added as such to the gasoline cuts to give a very high quality gasoline.

Dimerization of isobutene yields diisobutene which is a combination of 2,4,4-Trimethyl-1-pentene+2,4,4-Trimethyl-2-pentene as depicted in Scheme 3:

Scheme 3

Compounds that can be derived from the oligomerization of mixed butenes include but are not limited to: diisobutenes (DIBs), tri-isobutenes, dimer of isobutene and n-butenes, and trimer of isobutene and n-butenes. It will be appreciated by one of skill in the art that other products can be formed. As is known, DIB is a non-oxygenative fuel component with many advantages as a blending agent, such as higher RON, higher octane sensitivity or better anti-knock quality, higher energy content compared to MTBE and alkylates, and/or lower RVP than MTBE and ethanol.

Hydration/Oligomerization Process

As described herein, processes for production of mixed butanols (mixed alcohols) and butene oligomers from a hydrocarbon feed (mixed olefin feed) are provided as embodiments of the present disclosure. Additionally, processes for producing fuel compositions that include alcohols and oligomers prepared from butenes are also provided as embodiments of the present disclosure.

In one embodiment of the present disclosure, a process for producing alcohols and oligomers from mixed olefins is provided. More specifically, the process is one in which mixed olefins are simultaneously hydrated and oligomerized in the presence of water. A product stream that includes alcohols and butene oligomers is formed. In certain embodiments, the mixed olefin feed comprises a mixed butene feedstock and the product stream comprises mixed butanols and DIBs. In one embodiment, the product stream that includes mixed butanols and DIBs and can be combined with a fuel component to produce a fuel composition. The fuel component of the fuel composition can be selected from the group consisting of gasoline, diesel, jet fuel, aviation gasoline, heating oil, bunker oil, and any combination thereof. In certain embodiments, the resultant fuel composition will have increased RON and reduced RVP, without the presence of other chemicals that can have deleterious effects on the environment.

The source of the mixed olefin (e.g., mixed butene) stream can encompass any number of different sources of feedstocks (streams) that are suitable for use in the present disclosure. In some embodiments, the mixed olefin stream can be a refinery gas stream. In one embodiment, the mixed olefin stream can simply be a mixture of light olefins. As contemplated herein, the improved azeotropic separation system of the present disclosure accommodates a wider range of feedstocks than the prior art processes which were limited by the amount of isobutene in the feedstock. Thus, in some embodiments, the feedstock contains at least about 5 wt % of isobutene. In other embodiments, the feedstock contains at least about 10 wt % of isobutene. In other embodiments, the feedstock contains at least about 20 wt % of isobutene. In other embodiments, the feedstock contains at least about 40 wt % of isobutene. In other embodiments, the feedstock contains between about 5 wt % and about 50 wt % of isobutene. In other embodiments, the feedstock contains between about 10 wt % and about 50 wt % of isobutene. In other embodiments, the feedstock contains between about 20 wt % and about 50 wt % of isobutene. As used herein "wt %" means percent by weight.

Various types of olefins can be included in the mixed olefin stream. In some embodiments, the mixed olefin stream can include a mixed butene stream. In other embodiments, the mixed olefin stream includes pentenes, hexenes, propylene, n-butene, 2-butene, isobutene, olefins having more than 6 carbons with at least two butenes, or any combination thereof. Other olefins that can be used in accordance with other embodiments of the disclosure include, but are not limited to, ethylene, propene, pentenes, or other higher olefins. It will be understood that other suitable sources for the mixed olefin stream and types of olefins can be used so long as they are suitable for the intended application described herein and achieve a product stream having the desired characteristics that are set forth herein.

Non-limiting examples of olefin feedstocks that are suitable for use in the present disclosure include Raff1, Raff 2, Raff3, fluid catalytic cracking C4 (FCC C4), Crude C4 and any combination thereof. Each of these feedstock compositions contain mixed butenes and butadienes, namely 1-butene, isobutene, trans 2-butene, cis 2-butene, 1,3-butadiene and 1,2-butadiene, as well as C3-C5 alkanes/cycloalkanes and C5 alkenes/cycloalkenes.

In one representative but non-limiting embodiment, the mixed butene feed used in the present disclosure contains the four butene isomers in varying quantities as set forth in Table 1.

TABLE 1

| Components | Composition |
| --- | --- |
| n-butane | 4 |
| i-butane | 4 |
| 1-butene | 30 |
| i-butene | 43 |
| trans-2-butene | 11 |
| cis-2-butene | 8 |

Most commercial butene hydration processes utilize pure feeds of either 1-butene or isobutene, or mixed feeds for selective isobutene hydration. The process conditions are typically selected to maximize the yield of either 2-butanol or t-butanol. Because both 2-butanol and t-butanol are valuable oxygenates and octane enhancers for fuels, certain embodiments of the present disclosure utilize a system that is effective for the production of 2-butanol and t-butanol as primary reaction products.

Regarding the oligomerization of butenes, different butene isomers have different activities toward dimerization or oligomerization. For example, isobutene is more easily dimerized or oligomerized than n-butene. In accordance with one embodiment of the present disclosure, the present process is such that a portion of the isobutene in the feed is selectively oligomerized (dimerized) in the fixed bed reactor to form the two isomers of DIB (Scheme 3). Thus, in one embodiment, the resultant product stream includes the two isomers of DIBs as well as the butanols 2-butanol and t-butanol.

Similarly, regarding the hydration of butenes, the butene isomers vary in their hydration reaction rates. For example, the hydration reaction rates for both 2-cis and 2-trans-butene are significantly lower than that of 1-butene. Thus in accordance, with one embodiment of the present disclosure shown in FIG. 6, an isomerization unit is included in the system to convert 2-butenes into 1-butenes. The conversion of 2-butene isomers to 1-butene isomers can considerably enhance the hydration reactions, thereby increasing the single-pass conversion of mixed butenes to butanols.

Hydration/Oligomerization Catalyst

As described herein, mixed olefins are hydrated and oligomerized in a fixed bed reactor, in the presence of catalyst systems that are configured to perform the intended functions, namely, the hydration and oligomerization of mixed butenes, within one fixed bed reactor. It will be appreciated that the amount of catalyst can vary depending upon the mixed olefin stream being sent to the process. It will be appreciated that any number of suitable catalysts can be used for the hydration and oligomerization reactions so long as the catalyst operates in the manner described herein and achieves the intended objectives.

In some embodiments, the catalyst is of a type which hydrates the mixed olefin feedstock and oligomerizes at least a portion of the mixed olefin feedstock. More specifically, the catalyst is of a type and is selected so as to cause the oligomerization (dimerization) of a portion of the isobutene isomers (in the olefin feedstock) to DIBs, while the remaining mixed butenes are hydrated to butanols including the hydration of isobutene to form tert-butanol. As a result, the fixed bed reactor simultaneously hydrates the mixed butenes to form mixed butanols and selectively oligomerizes (dimerizes) a portion of the isobutene isomers to DIBs, and thus, the final product stream includes mixed butanols and DIBs.

In one embodiment, the hydration and oligomerization catalyst comprises an acidic catalyst. In one embodiment, the acidic catalyst is or comprises ionic exchange resins. Alternatively, the oligomerization catalyst and/or the hydration catalyst comprise substituted/non-substituted heteropoly acids or zeolites or any acidic solid acids. For example, a heteropoly acid (cesium substituted) can be prepared according to a process described in Miao Sun, et al., "Significant Effect on Acidity on Catalytic Behaviors of Cs-Substituted Polyoxometalates for Oxidative Dehydrogenation of Propone," Applied Catalysis A: General (2008); pp. 212-221, which is hereby incorporated by reference in its entirety. Commonly owned U.S. Pat. No. 9,498,772 which is hereby incorporated by reference in its entirety, sets forth catalysts that can be used as catalysts for use in the present disclosure. Commonly owned U.S. Pat. No. 10,293,332 and U.S. Patent Publication No. 2019/0194095, each of which is hereby incorporated by reference in its entirety, set forth framework-modified ultra-stable Y (USY) zeolite catalysts that can be used as catalysts for use in the present disclosure. The oligomerization catalyst and hydration catalyst can be the same or they can be different catalysts. Other catalyst system can be used so long as they achieve the objectives stated herein.

Embodiments of the Present Disclosure

In accordance with the present disclosure and as described in detail below and shown in the various figures, once the hydration and oligomerization (dimerization) reactions have occurred, various combinations of systems may be used to separate the product stream from the byproducts and unreacted olefins. In one embodiment illustrated in FIG. 1, after passing through a high-pressure (HP) separator (a "first separator"), the organic phase is sent to a debutenizer column (a "second separator") where the unreacted butenes are removed and recycled back to the fixed bed reactor. In some embodiments, the aqueous phase is sent from the high pressure separator to an azeotropic distillation column (a "third separator"). There, the alcohol-water azeotrope is distilled out of the aqueous phase and recycled back to the high-pressure separator for further recovery of alcohols (butanols), while the water is recycled upstream of the fixed bed reactor. Recycle pumps can be used to re-pressure recycled unreacted butenes and recycled water prior to their return to the system. In some embodiments, part of the alcohol-water azeotrope from the azeotropic distillation column and part of the unreacted butene stream from the debutenizer are purged to reduce inert build-up in the system ("purge streams"). The alcohol stream coming out of the debutenizer is sent to a product column ("a fourth separator") where pure sec-butyl alcohol (SBA) is extracted and a mixture of SBA, tert-butyl alcohol (TBA) and small quantities are produced. A portion of the SBA stream is mixed with the SBA/TBA stream to form a final composition, designated SuperButol™ fuel additive. Another portion of SBA is recycled back to the debutenizer to help break the azeotropic layer.

Figure 1:
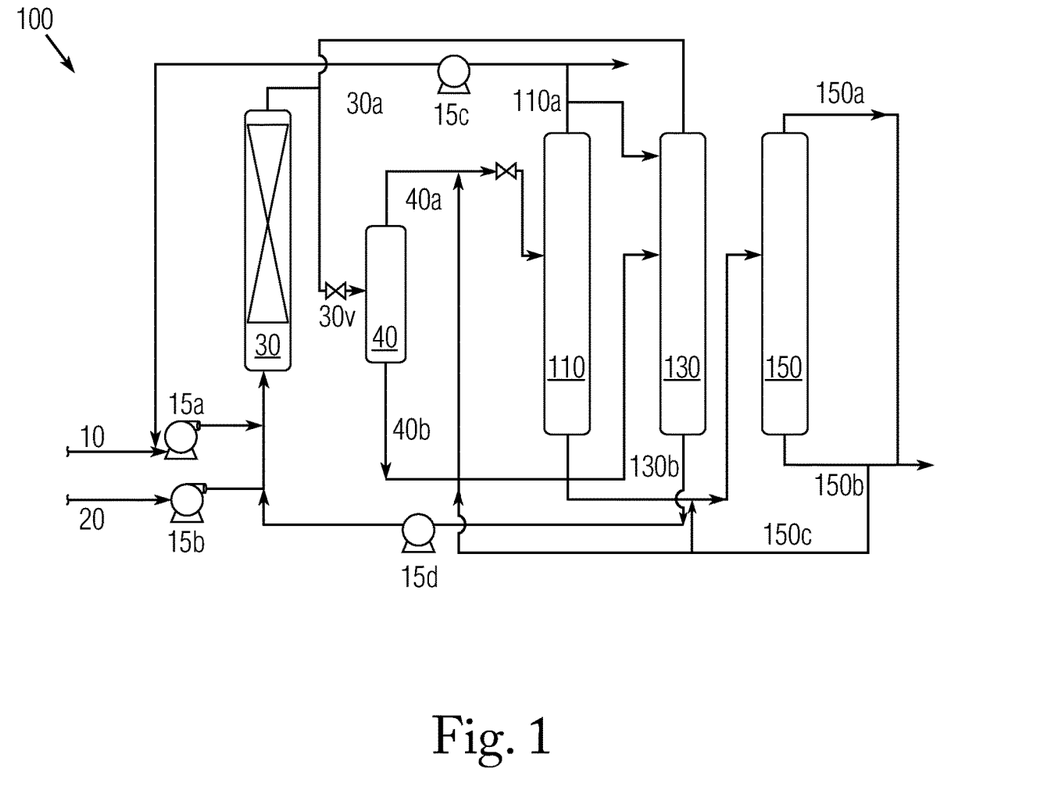
FIG. 1 shows a diagram of a process in accordance with a first embodiment of the present disclosure.

FIG. 1 illustrates one exemplary system 100 for performing the hydration and oligomerization of mixed olefins (butenes) in a process in accordance with a first embodiment of the present disclosure. FIG. 1 likewise shows an exemplary flow scheme. As described herein, at least the fixed bed reactor has an associated catalyst, and the remaining parts of the system 100 have associated equipment to produce the intended products.

The system 100 includes a fixed bed reactor 30 that serves as both a hydration reactor and an oligomerization reactor. The reactants are delivered to the fixed bed reactor 30 in the following manner A source of feedstock (e.g., a mixed olefin feed and more particularly, a mixed butene feed) 10 is fed to the fixed bed reactor 30. The reactor pressure and temperature can be varied using mixed butenes pump 15a, a downstream reactor pressure control valve 30v maintains the reactor pressure in the desired pressure. In one exemplary embodiment, the fixed bed reactor conditions are a pressure between about 10 bar and about 70 bar and a temperature between about 100° C. and about 190° C., respectively. A source of water 20 is added to this stream and pressurized to 10-70 bar using a pump 15b. The reactants are mixed then fed to the hydration reactor 30 configured to perform hydration and oligomerization of the feedstock introduced therein in the presence of water and under the operating conditions set forth above. The fixed bed reactor 30 can be in the form of a single stage reactor having an inlet to receive the feedstock 10 and water 20, and an outlet for product stream 30a. In the fixed bed reactor 30, n-butenes are hydrated to 2-butanol and isobutene is hydrated to tert-butanol, in the presence of a catalyst capable of initiating hydration and oligomerization reactions. For example, the catalyst can be located in one or more regions of the reactor 30.

The product stream 30a containing mixed butanols and DIBs exits the fixed bed reactor 30 and is introduced to a high-pressure separator 40 ("first separator"). In the high-pressure separator 40, the organic phase containing unreacted mixed butenes along with extracted mixed butanols is separated from the aqueous phase saturated with mixed butanols. The organic phase is removed through conduit 40a and sent to the debutenizer column 110 ("second separator") while the aqueous phase is removed through conduit 40b sent to azeotropic distillation column 130 ("third separator").

The organic phase, through conduit 40a, is then introduced to a debutenizer column 110, where unreacted mixed butenes are separated from a product stream. The debutenizer column 110 can be considered to be a second separator in the context of the claims. A debutenizer is a type of fractional distillation column used to separate butenes from other components during the refining process. Distillation is the process of heating a liquid to vapor and condensing the vapors back to liquid in order to separate or purify the liquid. Fractional distillation, as occurs in a debutenizer, is the separation of a fraction, i.e., a set of compounds that have a boiling point within a given range—from the rest of the mixture.

The unreacted butenes exit the debutenizer column 110 via conduit 110a, and recycled back to the fixed bed reactor 30 for further processing in the reactor 30. A recycle pump 15c may be included to re-pressurize the unreacted butenes prior to their recycle to fixed bed reactor 30. A portion of the unreacted butenes exiting the debutenizer 110 may purged from the system 100, if desired.

The aqueous phase exiting the high-pressure separator 40 via conduit 40b is transferred to an azeotropic distillation column 130. The azeotropic distillation column 130 can be considered to be a third separator in the context of the claims. In the azeotropic distillation column 130, the alcohol-water azeotrope is distilled out of the aqueous phase and recycled back to the high-pressure separator 40 to further recover the alcohols (butanols). A part of the alcohol-water azeotrope recovered from column 130 can be purged to reduce inert build-up in the system. Water exits the azeotropic distillation column through conduit 130b and recycled back upstream of the fixed bed reactor 30. A recycle pump 15d re-pressurizes the water prior to its recycling to the fixed bed reactor 30.

The alcohols stream in 110a coming out of debutenizer 110 is sent to a product column 150 where pure SBA is extracted in stream 150b and a mixture of TBA, SBA and small quantity of water 150a is produced. The product column 150 can be considered to be a "fourth separator" in the context of the claims. In one embodiment, a portion of SBA stream 150b is mixed with stream 150a to form the final composition of SuperButol™ fuel additive. Another portion of SBA stream==150 cis sent back to the debutenizer column 110 to help break the azeotropic layer.

According to the principles of the present disclosure, product column 150 functions to separate SBA from TBA and DIB. This, in turn, enables recycling of the SBA stream to the debutenizer column in order to tilt the azeotropic curve and improve the TBA/water separation, which consequently reduces the required energy for the rebuilder/cooler in the debutenizer column. Thus, by utilization of product column 150, the water content in the organic stream leaving the debutenizer is substantially decreased from about 4.5-5 wt % to less than about 0.5 wt %.

Moreover, advantageously, use of product column 150 provides flexibility in generating a desired SuperButol™ composition where the ratio of SBA to TBA may be altered to meet changing fuel specifications due to, e.g., seasonal changes. For example, TBA forms crystals in cold weather when constituting the majority of SuperButol™ composition. The process of the present disclosure obviates this issue by allowing the use to vary the TBA/SBA composition as desired.

Alternatively, the present process can be used to generate pure SBA for additional uses as known in the art, e.g., in a methyl ethyl ketone (MEK) plant.

It will be appreciated that this final product, which can be considered to be a product stream of RON enhanced mixed butanols and DIBs, can then undergo additional processing and/or transportation to another site, such as a storage site.

The process and system described herein differ from the process of U.S. Pat. No. 9,732,018 at least in two respects. First, according to the '018 patent, the final product from the debutenizer column does not undergo further purification and is used as is. However, as mentioned above, the prior art processes are limited in the amount of isobutene feed that can be used. This is due in part to the high affinity of TBA to water. In contrast, according to the present disclosure, the mixed butanol from the debutenizer column 110 undergoes a further processing step in a fourth separator, e.g., product column 150 to produce the final product. Moreover, the present disclosure includes a step of recycling of SBA to enhance azeotropic separation of water and TBA (FIG. 1, 150c). These improvements tilt the azeotropic distillation curve to extract water more easily. Thus, the new process provides a technical advantage in that it permits the use of higher quantity of isobutene while still resulting in on-specification products. In turn, this, allows for use of a wider range of olefin feedstock compositions than in the prior art.

The process and system described herein differ from the process of U.S. Pat. No. 8,999,013 for the same reasons outlined above, and further on the grounds that the '013 patent does not use an azeotropic distillation unit to separate butanol/DIB products from water.

Figure 2:
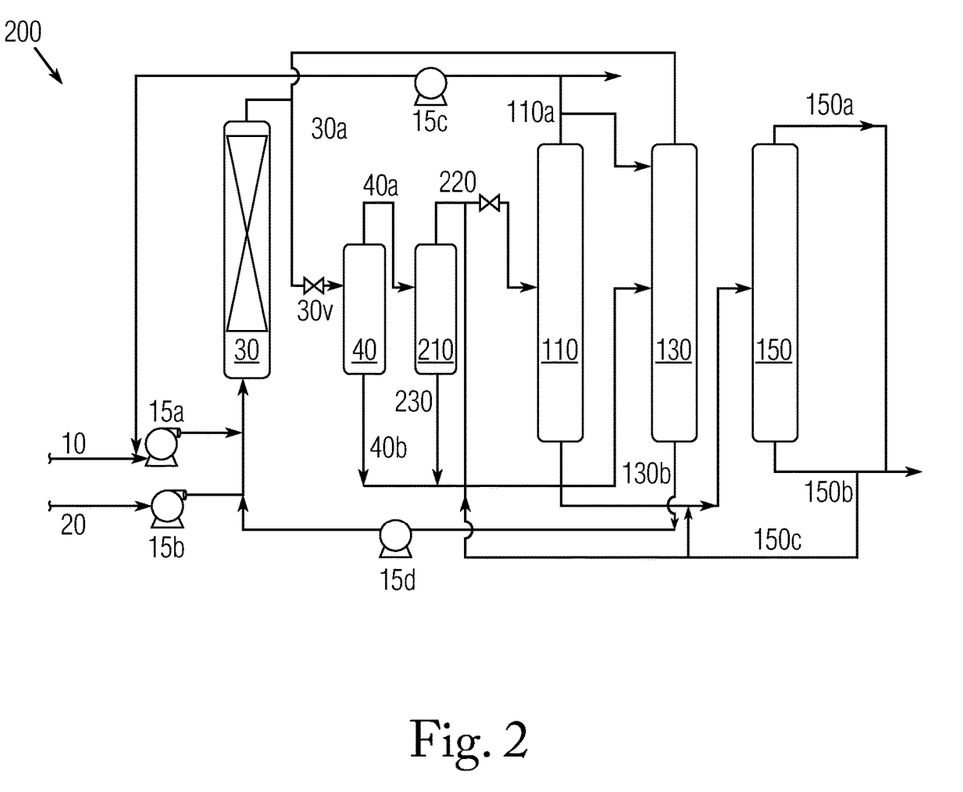
FIG. 2 shows a diagram of a process in accordance with a second embodiment of the present disclosure.
Figure 3:
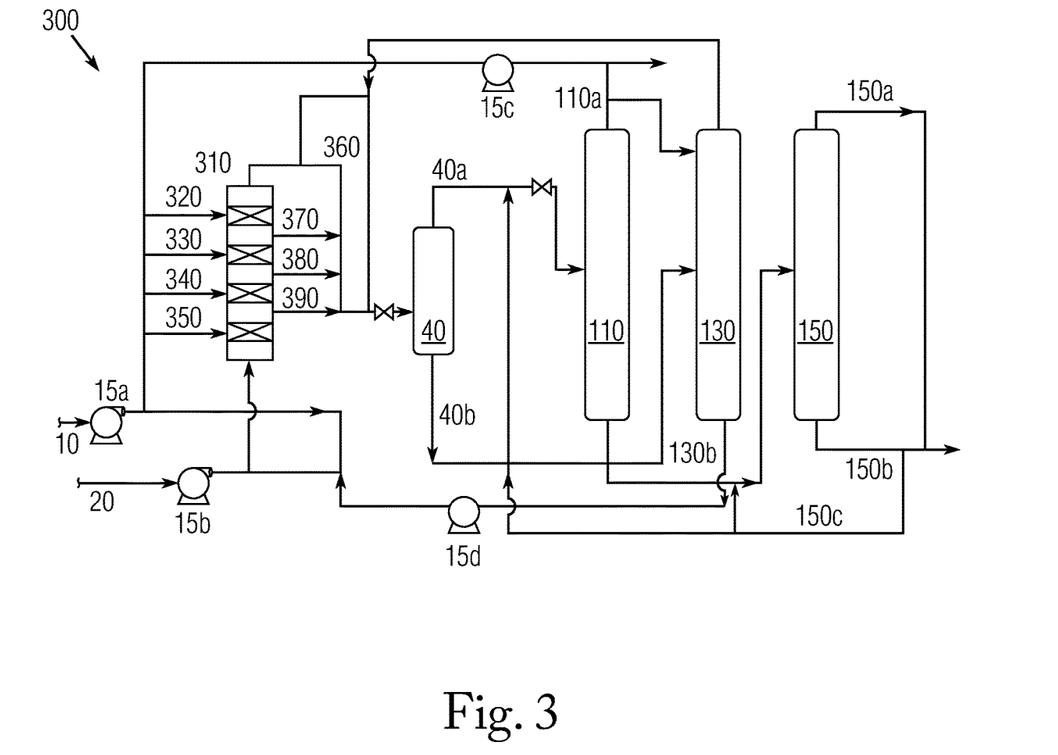
FIG. 3 shows a diagram of a process in accordance with a fifth embodiment of the present disclosure.
Figure 4:
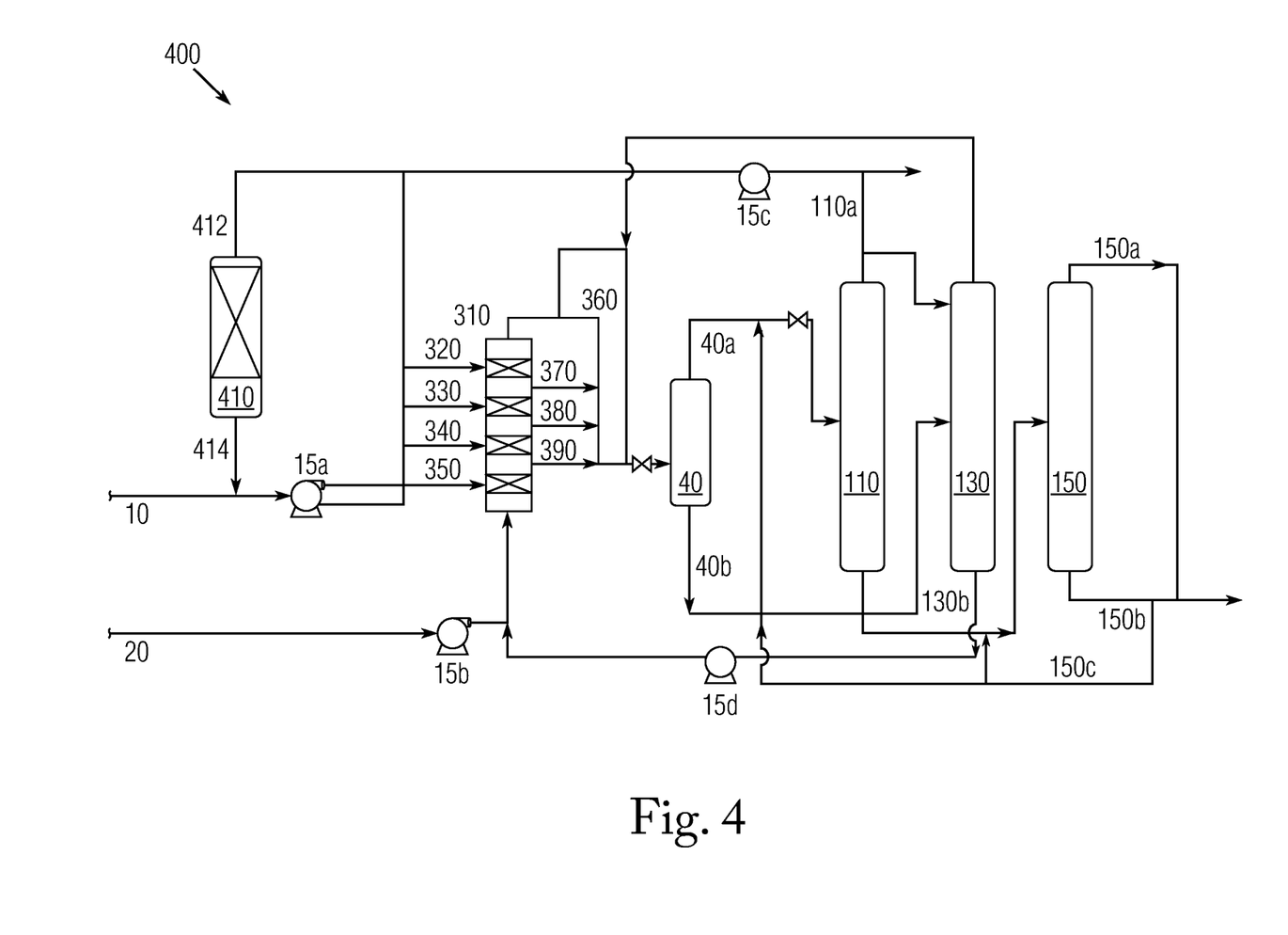
FIG. 4 shows a diagram of a process in accordance with a sixth embodiment of the present disclosure.

In embodiments of the disclosure other separation techniques can be used as described below. In FIGS. 2-4, like elements are numbered alike and the discussion of FIGS. 2-4 is focused on the differences between the separation techniques to enhance the yield and purity of the final product.

FIG. 2 describes a second embodiment of the present disclosure. FIG. 2 features a system 200 which adds a low pressure separator 210 downstream of the high pressure separator 40 described in FIG. 1. According to this embodiment, the product stream 30a from the fixed bed reactor 30 is first sent from the fixed bed reactor to a high-pressure separator 40, where the organic phase of the product stream containing unreacted mixed butenes and extracted mixed butanols is separated from the aqueous phase. The organic phase 40a coming out of the high pressure separator 40 is then sent to a low-pressure separator 210 for removal of additional water. The organic phase (unreacted butenes and extracted butanols) then exits the low pressure separator via conduit 220, and the water (aqueous phase) is removed from the low-pressure separator via conduit 230. The combined high and low-pressure separators can be considered to be a "first separator" as set forth in the claims. The organic phase 220 is then introduced into debutenizer 110 as described in FIG. 1.

FIG. 3 illustrates a third separation scheme according to the present disclosure. FIG. 3 features a system 300 in which, the feed source 10 is connected to a multi-stage reactor 310. In the embodiment illustrated in FIG. 3, the multi-stage reactor 310 can replace the main fixed bed reactor 30 in the system 100 of FIG. 1. The different stages of the multi-stage reactor 310 each have an intermittent feed supply and product separation modules to enhance the single-pass mixed butenes conversion. More specifically, each stage of the reactor 310 has an entrance for their respective feeds and an exit for their respective products, and each of the product streams is then be sent to the high-pressure separator 40. In FIG. 3, there are four inlet conduits (entrances) 320, 330, 340, 350 and there are associated exits 360, 370, 380, and 390 which correspond to the respective three stages.

As contemplated herein, the overall single-pass conversion rate is significantly increased with the use of the multi-stage reactor 310, thereby reducing the recycling flow rate and the capital costs of the equipment. In one currently preferred embodiment, there are three stages in the multi-stage reactor 310; however, in other embodiments, more stages can be employed to further increase the single-pass conversion rate.

FIG. 4 illustrates a fourth separation scheme according to the present disclosure. FIG. 4 features a sixth separation system 400, in which the system performance is enhanced with a 2-butenes to 1-butenes isomerization unit 410. The isomerization unit 410 is configured such that 2-butenes are converted into 1-butenes prior to entering the multi-stage reactor 310. As shown, the unit 410 includes an exit conduit 414 that is in fluid communication with olefin feed 10 for delivering 1-butenes to the reactor 310. Furthermore, an inlet of the unit 410 is fluidly connected to a conduit 412 which connects to the debutenizer 110 and receives the unreacted butenes therefrom.

Because the hydration reaction rate of 1-butenes is significantly higher than that of 2-butenes, the addition of a "2-butene to 1-butene" isomerization unit further enhances the single-pass conversion rate of the mixed butene feed since the concentration of 1-butenes in the feedstock is increased, while the concentration on 2-butenes is decreased.

Use of as Fuel Components

As contemplated herein, the products of the present disclosure can be used as superior gasoline constituents without further separation. The mixed butanols serve as oxygenated octane enhancers to provide for increased combustion efficiency, thereby reducing emissions. The DIBs complement the mixed butanols by serving as high energy content octane enhancers and low RVP gasoline components.

The advantageous qualities of butanols and DIBs as gasoline components compared with other known gasoline components are further explained by the data in Table 2. This data stems from an experiment in which the five compounds listed below (MTBE, ethanol, 2-butanol, t-butanol, and DIB) are each blended into a base gasoline in concentrations of 5, 10, 15, 20, and 25%, respectively, and their respective characteristics are determined. In particular, Table 2 sets forth the trends in RON, Mon, octane sensitivity, and RVP, respectively.

TABLE 2

Properties comparison for various blends

| Component | Blending RON | Blending MON | Blending Sensitivity | Energy Density or HHV (MJ/Kg) | RVP 15% v/v Blend |
|---|---|---|---|---|---|
| Base gasoline | 85.8 | 81.0 | 4.8 | 45.6 | 9.46 |
| MTBE | 124.7 | 103.5 | 21.2 | 38.0 | 9.6 |
| Ethanol | 139.8 | 106.6 | 33.2 | 29.9 | 11.5 |
| 2-Butanol | 116.6 | 97.8 | 18.8 | 37.3 | 10.4 |
| tert-butanol | 108.6 | 89.3 | 19.3 | 37.3 | 9.96 |
| DIBs | 132.1 | 99.2 | 32.9 | 48.2 | 8.5 |

As shown by Table 2, compared with other common fuel constituents, DIB has the lowest RVP, the highest energy density, the second highest blending RON, and the second highest blending octane sensitivity (essentially equivalent to that of ethanol). Additionally, 2-butanol and t-butanol have blending octane sensitivities and energy densities comparable to MTBE, and result in a lower RVP at 15% concentrations than ethanol. Based on this data, it can be inferred that the combination of butanols and DIBs creates a high-octane fuel additive with the potential to replace ethanol as a superior oxygenate. The present disclosure allows for high-yield, on-specification production of a mixed butanols and DIB product through the process scheme described herein.

Thus, in some embodiments, the alcohols and dimers in the product stream made in accordance with the embodiment of the present disclosure can be used as a component in fuel compositions or as a neat fuel composition. For example, in one embodiment, a neat fuel composition can be prepared according to the methods described herein that include a mixed butanol fuel having an octane rating suitable for use in combustion or compression engines. In another embodiment, a fuel composition that includes a fuel component and a mixed butanol fuel is provided. In an embodiment, the fuel component can include jet fuel, gasoline, aviation gasoline, diesel, heating oil, bunker oil, and any combination thereof. In an aspect, the mixed butanols can include n-butanol, 2-butanol, iso-butanol, t-butanol, and any combination thereof; or alternatively, 2-butanol and t-butanol. In certain embodiments, the mixed butanols can include at least two butanol compounds selected from n-butanol, 2-butanol, iso-butanol, t-butanol, and any combination thereof; or alternatively, 2-butanol and t-butanol.

The mixed alcohols (butanols) stream made in accordance with the various embodiments of the present disclosure can be also used in other types of fuel compositions, as will be apparent to those skilled in the art and are to be considered within the scope of the present disclosure.

The process and the system of the present disclosure provide a number of advantages over conventional hydration and oligomerization/dimerization processes. These advantages include but are not limited to: (1) allowing the use of a wider range of olefin feedstock which contains higher amounts of isobutene (e.g., at least about 5% by weight, at least about 10% by weight, at least about 20% by weight etc.), while still achieving on-specification products; (2) providing higher purity in the composition of the mixed butanols/DIBs final product than previous methods for simultaneously hydrating and oligomerizing mixed olefin feeds; (3) providing a higher rate of single-pass conversion of the mixed butenes feed to mixed butanols and DIBs; (4) providing an alternative gasoline oxygenate that possesses comparable RON enhancement properties and higher energy content than MTBE and ethanol, while eliminating the associated compatibility and contamination issues; and (5) utilizing the products of the present disclosure—namely, mixed butanols and DIBs—as superior gasoline constituents without separation.

EXAMPLES

The following examples are provided to better illustrate embodiments of the present disclosure. However, it is to be understood that these examples are merely illustrative in nature, and that the process embodiments of the present disclosure are not necessarily limited thereto.

Example 1

The process of the present disclosure was carried out with an Aspen distillation column system to generate a product stream as described in Table 3 below. The 2-Reactor system is a reference system lacking product column 150. The 3-Reactor system includes product column 150 in accordance with the principles of the present disclosure.

TABLE 3

| | | | 2-Reactors | 3-Reactors AFW |
|---|---|---|---|---|
| Feed | Btm | N-BUTANE | 76.31 | 17.02 |
| | | ISOBUTANE | 30.70 | 16.67 |
| | | 1-BUTENE | 182.24 | 124.41 |
| | | ISOBUTYLENE | 218.70 | 182.11 |
| | | TRANS-2-BUTENE | 74.49 | 45.45 |
| | | CIS-2-BUTENE | 56.99 | 33.63 |
| | | TERT-BUTYL-ALCOHOL | 23.92 | 0.01 |
| | | 2-BUTANOL | 4.01 | 0.00 |
| | | 2,4,4-TRIMETHYL-1-PENTENE | 0.03 | 0.00 |
| | | 2,4,4-TRIMETHYL-2-PENTENE | 0.62 | 0.00 |
| | | BUTYL-ETHER | 0.00 | 0.00 |
| | | WATER | 921.43 | 619.05 |
| Reactor effluent (stream 30a, FIGS. 1-4) | Btm | N-BUTANE | 76.31 | 17.02 |
| | | ISOBUTANE | 30.70 | 16.67 |
| | | 1-BUTENE | 137.30 | 93.73 |
| | | ISOBUTYLENE | 89.22 | 74.29 |
| | | TRANS-2-BUTENE | 67.75 | 41.39 |
| | | CIS-2-BUTENE | 54.20 | 32.28 |
| | | TERT-BUTYL-ALCOHOL | 165.96 | 118.28 |
| | | 2-BUTANOL | 75.97 | 46.91 |
| | | 2,4,4-TRIMETHYL-1-PENTENE | 16.44 | 13.67 |
| | | 2,4,4-TRIMETHYL-2-PENTENE | 6.18 | 4.63 |
| | | BUTYL-ETHER | 0.00 | 0.66 |
| | | WATER | 869.41 | 578.81 |

TABLE 3-continued

| | | | 2-Reactors | 3-Reactors AFW |
|---|---|---|---|---|
| Low Pressure Separator (V-61) Column 210 (FIG. 2) Top: feed 220 to debutenizer 110 (FIG. 2) Bottom: feed 230 to column 130 (FIG. 2) | Top | N-BUTANE | 166.20 | 86.96 |
| | | ISOBUTANE | 40.40 | 85.17 |
| | | 1-BUTENE | 180.66 | 415.59 |
| | | ISOBUTYLENE | 117.39 | 242.37 |
| | | TRANS-2-BUTENE | 89.14 | 201.58 |
| | | CIS-2-BUTENE | 71.32 | 160.63 |
| | | TERT-BUTYL-ALCOHOL | 143.38 | 148.09 |
| | | 2-BUTANOL | 71.98 | 65.92 |
| | | 2,4,4-TRIMETHYL-1-PENTENE | 16.46 | 17.15 |
| | | 2,4,4-TRIMETHYL-2-PENTENE | 6.59 | 8.45 |
| | | BUTYL-ETHER | 0.00 | 0.00 |
| | | WATER | 21.66 | 26.63 |
| | Btm | N-BUTANE | 0.05 | 0.04 |
| | | ISOBUTANE | 0.01 | 0.04 |
| | | 1-BUTENE | 0.06 | 0.25 |
| | | ISOBUTYLENE | 0.05 | 0.17 |
| | | TRANS-2-BUTENE | 0.03 | 0.13 |
| | | CIS-2-BUTENE | 0.03 | 0.10 |
| | | TERT-BUTYL-ALCOHOL | 2.68 | 4.86 |
| | | 2-BUTANOL | 0.48 | 0.93 |
| | | 2,4,4-TRIMETHYL-1-PENTENE | 0.00 | 0.00 |
| | | 2,4,4-TRIMETHYL-2-PENTENE | 0.00 | 0.00 |
| | | BUTYL-ETHER | 0.00 | 1.89 |
| | | WATER | 26.18 | 81.90 |
| T-201 (debutenizer-column 110) | Top | N-BUTANE | 166.20 | 86.96 |
| | | ISOBUTANE | 40.40 | 85.17 |
| | | 1-BUTENE | 180.66 | 415.59 |
| | | ISOBUTYLENE | 117.39 | 242.37 |
| | | TRANS-2-BUTENE | 89.14 | 201.58 |
| | | CIS-2-BUTENE | 71.32 | 160.63 |
| | | TERT-BUTYL-ALCOHOL | 2.24 | 1.61 |
| | | 2-BUTANOL | 0.03 | 0.52 |
| | | 2,4,4-TRIMETHYL-1-PENTENE | 0.08 | 0.10 |
| | | 2,4,4-TRIMETHYL-2-PENTENE | 1.73 | 3.33 |
| | | BUTYL-ETHER | 0.00 | 0.00 |
| | | WATER | 16.88 | 43.98 |
| | Btm | N-BUTANE | 0.00 | 0.00 |
| | | ISOBUTANE | 0.00 | 0.00 |
| | | 1-BUTENE | 0.00 | 0.00 |
| | | ISOBUTYLENE | 0.00 | 0.00 |
| | | TRANS-2-BUTENE | 0.00 | 0.00 |
| | | CIS-2-BUTENE | 0.00 | 0.00 |
| | | TERT-BUTYL-ALCOHOL | 141.14 | 159.42 |
| | | 2-BUTANOL | 71.95 | 260.28 |
| | | 2,4,4-TRIMETHYL-1-PENTENE | 16.38 | 39.91 |
| | | 2,4,4-TRIMETHYL-2-PENTENE | 4.86 | 5.22 |
| | | BUTYL-ETHER | 0.00 | 12.17 |
| | | WATER | 4.78 | 0.96 |
| n-C4 & i-C4 | Purge | N-BUTANE | 66.48 | 17.02 |
| | | ISOBUTANE | 16.16 | 16.67 |
| | Product | N-BUTANE | 0.00 | 0.00 |
| | | ISOBUTANE | 0.00 | 0.00 |
| Product stream (resulting from product column 150) | Product | SBA | | 61.80 |
| | | TBA | | 27.40 |
| | | DIB | | 9.50 |
| | | WATER | | 0.40 |

As seen, the addition of SBA to debutenizer column T-201 in the 3-reactor system aids in the separation of TBA/SBA and water. This further has substantial effect on the column duties of the reboiler and cooler. The water content in the organic stream exiting the debutenizer is greatly reduced form 4.78 wt % to 0.4 wt %.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A process for simultaneously hydrating and oligomerizing a hydrocarbon feed comprising mixed olefins, the process comprising the steps of:
   a) contacting the hydrocarbon feed with water and a catalyst in a fixed bed reactor, wherein the catalyst hydrates the mixed olefins to form mixed alcohols and oligomerizes at least a portion of the mixed olefins into oligomers, to produce a first stream comprising an organic phase and an aqueous phase;
   b) introducing the first stream into a first separator that separates the organic phase from the aqueous phase;
   c) introducing the separated organic phase from step (b) into a second separator that separates unreacted olefins from mixed alcohols and one or more oligomers to produce a second stream comprising mixed alcohols and one or more oligomers;
   d) introducing the separated aqueous phase from step (b) into a third separator that separates an alcohol-water azeotrope component from water;
   e) introducing the second stream from step (c) into a fourth separator which extracts sec-butyl alcohol (SBA) to produce an SBA stream, and a third stream comprising mixed butanols and one or more oligomers;
   f) mixing the third stream obtained in step (e) with a first portion of the SBA stream obtained in step (e) to produce a final product stream; and
   g) recycling a second portion of the SBA stream produced in step (e) to the second separator.

2. The process of claim 1, wherein the final product stream comprises mixed butanols and diisobutene (DIB).

3. The process of claim 2, wherein the final product stream comprises tert-butanol (TBA), sec-butanol (SBA) and diisobutene (DIB).

4. The process of claim 1, wherein the mixed olefin feed comprises 10 wt % or greater isobutene.

5. The process of claim 1, wherein the mixed olefin feed comprises 20 wt % or greater isobutene.

6. The process of claim 1 wherein the portion of SBA stream that is recycled to the second separator in step (g) breaks an azeotropic layer in the second separator.

7. The process of claim 1, wherein the mixed olefins comprise mixed butenes selected from the group consisting of 1-butene, 2-trans-butene, 2-cis-butene, isobutene and any combination thereof.

8. The process of claim 1, wherein the mixed alcohols produced in step (a) comprise mixed butanols selected from the group consisting of 1-butanol, 2-butanol (sec-butanol), iso-butanol, tert-butanol, and mixtures thereof.

9. The process of claim 1, further comprising the steps of adjusting a pressure and temperature of the hydrocarbon feed and adjusting a pressure and temperature of the water.

10. The process of claim 9, wherein a pressure of the fixed bed reactor is between about 10-70 bar, and the temperature of the fixed bed reactor is between about 100-160° C.

11. The process of claim 1, wherein the first separator comprises a high-pressure separator configured to separate the organic phase from the aqueous phase.

12. The process of claim 1, wherein the first separator comprises a high-pressure separator and a low pressure separator that are arranged in series with the low-pressure separator being downstream of the high-pressure separator, wherein each of the high and low-pressure separators is configured to separate the organic phase from the aqueous phase.

13. The process of claim 1, wherein the second separator comprises a debutenizer which removes unreacted butenes.

14. The process of claim 1 or 13, further comprising the step of recycling the unreacted butenes to the fixed bed reactor.

15. The process of claim 1, wherein the third separator comprises an azeotropic distillation column in which the alcohol-water azeotrope is distilled out of the aqueous phase and recycled back to the first separator and water is recycled back to the fixed bed reactor.

16. The process of claim 1, further comprising the step of combining the final product stream with a gasoline stream to produce a gasoline product with reduced Reid vapor pressure (RVP) and increased research octane number (RON) compared with the gasoline stream alone.

17. The process of claim 1, wherein the catalyst present in the fixed bed reactor comprises an ion exchange resin catalyst.

18. The process of claim 1, wherein the fixed bed reactor comprises a multi-stage reactor, with each stage having an individual feed line that receives the hydrocarbon feed and an individual exit line that communicates with a common line that delivers the first product stream to the first separator.

19. The process of claim 1, further including an isomerization unit that is fluidly connected between the second separator and the fixed bed reactor and that receives the unreacted olefins from the second separator and serves to convert the unreacted olefins from a first isomer to a second isomer prior to introduction into the fixed bed reactor.

20. The process of claim 19, wherein the isomerization unit comprises a 2-butenes to 1-butenes isomerization unit and wherein the first isomer comprises 2-butenes and the second isomer comprises 1-butenes.

21. The process of claim 1, further comprising the step of isolating pure sec-butyl alcohol (SBA) after step (e).

* * * * *